United States Patent
Cote-Sierra et al.

(10) Patent No.: US 10,376,475 B2
(45) Date of Patent: Aug. 13, 2019

(54) METHOD OF USE

(71) Applicant: Dermavant Sciences GmbH, Basel (CH)

(72) Inventors: Javier Cote-Sierra, Research Triangle Park, NC (US); Susan H. Smith, Research Triangle Park, NC (US); Steven M. Frey, Research Triangle Park, NC (US)

(73) Assignee: DERMAVANT SCIENCES GMBH, Basel (CH)

( * ) Notice: Subject to any disclaimer, the term of this patent is extended or adjusted under 35 U.S.C. 154(b) by 0 days.

(21) Appl. No.: 15/529,671

(22) PCT Filed: Dec. 9, 2015

(86) PCT No.: PCT/IB2015/059490
§ 371 (c)(1),
(2) Date: May 25, 2017

(87) PCT Pub. No.: WO2016/092493
PCT Pub. Date: Jun. 16, 2016

(65) Prior Publication Data
US 2017/0360719 A1   Dec. 21, 2017

Related U.S. Application Data

(60) Provisional application No. 62/090,908, filed on Dec. 12, 2014.

(51) Int. Cl.
*A61K 31/05* (2006.01)
*A61K 9/00* (2006.01)
*A61K 45/06* (2006.01)

(52) U.S. Cl.
CPC ............ *A61K 31/05* (2013.01); *A61K 9/0014* (2013.01); *A61K 45/06* (2013.01)

(58) Field of Classification Search
CPC ...... A61K 31/05; A61K 45/06; A61K 9/0014; A61K 2300/00
See application file for complete search history.

(56) References Cited

U.S. PATENT DOCUMENTS 9,308,239 B2 *  4/2016  Thiboutot ............ A61K 31/575
2005/0059733 A1  3/2005  Chen et al.

OTHER PUBLICATIONS

Gessner, Neurodermitis-Sonnenblumenöl hilft Steroid einsparen: Medical Tribune—Medizin und Gesundheit. retrieved online at: http://www.medical-tribune.de/medizin/fokus-medizin/artikeldetail/neurodermitis-sonnenblumenoel-hilft-steroid-einsparen.html. (2011).
Kelhälä et al., IL-17/Th17 pathway is activated in acne lesions. PLoS One. Aug. 25, 2014;9(8):e105238.

* cited by examiner

*Primary Examiner* — Zohreh A Fay
(74) *Attorney, Agent, or Firm* — Pepper Hamilton LLP (57) ABSTRACT

The present invention relates to a novel method of treatment of acne in a human patient in need thereof, comprising administering topically to said patient an effective amount of the compound 3,5-Dihydroxy-4-isopropyl-trans-stilbene (Compound 1) or a pharmaceutically acceptable salt thereof.

30 Claims, 6 Drawing Sheets

METHOD OF USE

FIELD OF THE INVENTION

The present invention relates to the novel use of a stilbene derivative for the treatment of acne vulgaris.

BACKGROUND OF THE INVENTION

Acne vulgaris (or simply acne) is a common skin condition affecting an estimated 650 million people, or 9.4% of the population, worldwide. (Vos et al. Lancet, 380(9859): 2163-2196, 2012) The condition, characterized by areas of skin with seborrhea, comedones, papules, nodules, pimples, and possible scarring, often occurs in adolescences, but may persists much further into adulthood (James. N Engl J Med, 352(14):1463-1472, 2005).

Adolescence is a period of high social insecurity, and the appearance of and potential scarring from acne often result in psychological issues such as reduced self-esteem, depression, or, in extreme cases, suicide (Goodman. Aust Fam Physician, 35(7):503-504, 2006; Purvis et al. J Paediatr Child Health, 42(12):793-796, 2006).

An immunological reaction to the gram-positive microbe *Propionibacterium acnes* (*P. acnes*) is implicated in playing a major role in the initiation of the acute inflammatory response in patients (De Young et al. J Invest Dermatol, 83(5):394-398, 1984; Jappe et al. Br J Derm. 146(2):202-209, 2002). Acne treatments work by reducing sebum production by sebocytes, speeding up cell turnover, fighting bacterial infection, reducing inflammation, or some combination of these strategies. Treatment of acne tends to be long and primarily focuses on the use of retinoids, benzoyl peroxide, and antibacterials—particularly oral tetracyclines and topical clindamycin. In addition to the growing rate in the resistance of *P. acnes* to these treatments, recently the usefulness of eradication of *P. acnes*, a commensal bacteria found in most healthy human skin, as a primary target for therapy in acne has been questioned, and instead some are considering a model based on treatment of the inflammatory response to the bacteria (Agak et al. J Invest Dermatol, 2013). Inflammation is clinically associated in late stages of acne with the presence of inflamed papules and pustules and histologically by the presence of cell infiltrates in open comedones (Tanghetti, E. A. J. Clin. and Aesthetic Derm. 6(9):27-35, 2013). In the past decade, new findings have demonstrated the involvement of inflammatory mechanisms as part of the pathogenesis of early acne (Norris, J. F. and et al. Br. J. Dermatol. 118:651-659, 1988) and the evolving view is that acne should be regarded as an inflammatory disease (Stein, L. F. and et al. J. Drugs Dermatol. Suppl 6:s67-s69, 2013). In fact, the skin is an immunologically active organ. Follicular keratinocytes and sebocytes, the main constituents of the pilosebaceous unit, activate the innate immune system by recognizing *P. acnes*. Both inter-follicular and infundibular human keratinocytes and sebocytes can sense the presence of *P. acnes* as they express functional Toll-like receptor (TLR) 2, TLR4 and CD14, consistent with the role of these cells in innate immunity (Song, P. I. et al. J. Invest Dermatol. 119:424-432, 2002; Selway, J. L. et al. BMC Dermatol. 13:10, 2013; Nagy et al. Microbes and Infection, 8:2195-2205, 2006). In fact, *P. acnes*, a gram-positive bacteria, may trigger the immune system in early and late acne lesions through the activation of TLR2 by the pathogen associated molecular patterns (PAMPs) such as peptidoglycan (PGN) and Lipoteichoic acid (LTA). Indeed, IL-1a is released by keratinocytes in response to TLR2 activation. Similarly, PGN and LTA cause keratinocyte hypercornification, which is characteristic of acne lesions. It has also been shown that *P. acnes* induces the secretion of Th1 and proinflammatory cytokines (IFNγ, IL-12, IL-18, IL-8, and IL-1b) in human monocytes, suggesting that *P. acnes* may activate tissue macrophages that surround pilosebaceous follicles (Sugisaki, H. et al. J. Dermatol. Sci. 55(1):47-52, 2009; Kim, J. Dermatology. 211 (3):193-198, 2005). Finally, recent studies have shown that *P. acnes* stimulated the expression of Th17-related genes, including IL-17A, RORα, RORγ, IL-17RA and triggered the secretion of IL-17 from CD4 T cells (Agak et al. J Invest Dermatol, February 2014 134(2): 366-73). Therefore, because inflammation is present in both early and late acne lesions, anti-inflammatory therapies are proposed as able to clear acne lesions regardless which etiologic factor is involved in the initiation or maintenance of acne lesions.

The usefulness of commercially available purely anti-inflammatory compounds is limited due to safety concerns with respect to the prolonged use of corticosteroids, and retinoids and vitamin D analogs. Additionally anti-inflammatory treatments can have other effects on sebum production, bacterial populations, and skin turnover.

Thus, there remains a need for safer and more efficacious therapies for use in the treatment of acne. A treatment which is safe, efficacious, and anti-inflammatory by a novel pathway that does not have the same safety concerns as current anti-inflammatory treatments would be an inventive addition to acne treatment regimens.

DESCRIPTION OF THE DRAWINGS

FIG. 3 (A-C) shows 3,5-Dihydroxy-4-isopropyl-trans-stilbene suppresses cytokine secretion by differentiated Th17 cells and potently inhibits the Th17 polarization of CD4+ T cells.

SUMMARY OF THE INVENTION

The invention provides a method for the treatment of acne using the anti-inflammatory compound 3,5-Dihydroxy-4-isopropyl-trans-stilbene (1) or a pharmaceutically acceptable salt thereof.

Another aspect of the invention is the topical application to the patient for the treatment of acne with the compound 3,5-Dihydroxy-4-isopropyl-trans-stilbene or a pharmaceutically acceptable salt thereof.

Another aspect of the invention is the once daily topical application to the patient for the treatment of acne with the compound 3,5-Dihydroxy-4-isopropyl-trans-stilbene or a pharmaceutically acceptable salt thereof.

In another embodiment, the compound 3,5-Dihydroxy-4-isopropyl-trans-stilbene, or a pharmaceutically acceptable salt thereof, is useful for the topical treatment of acne.

DETAILED DESCRIPTION OF THE INVENTION

The compound 3,5-Dihydroxy-4-isopropyl-trans-stilbene, or a pharmaceutically acceptable salt thereof is also known as 5-[(E)-2-phenylethenyl]-2-(propan-2-yl)benzene-1,3-diol, or 2-(1-Methyethyl)-5-[(1E)-2-phenylethenyl]-1,3-benzenediol, and also referred to herein as compound 1, has the following structure:

The synthesis of 3,5-Dihydroxy-4-isopropyl-trans-stilbene is known, and has further been studied by a number of researchers, see Krow, G. R. et al. JOC, 57(14):4040-4043, 1992; Azzena, U. et al. Synthetic Communications 33(8):1309-1317, 2003; Gao, J. et al., Advanced Materials Research 236-238:2378-2382, 2011. Various patent applications by the University of Hebei Sci & Technology have also been filed on the synthesis of this compound, see CN 101531571 (2009); CN 101633606 (2010); CN 101648851 (2010); CN 101830764 (2010); and CN 101838173 (2010).

A biosynthetic pathway for production of stilbenes, including 1, by *Photorhabdus*, has also been proposed, see Joyce, S. A. et al., Angewandte Chemie Int. Ed. 47:1942-1945, 2008. The compound 3,5-Dihydroxy-4-isopropyl-trans-stilbene is believed to have been originally disclosed by Paul, V. et al., Journal of Chemical Ecology 7(3):589-597, 1981 as an antibiotic. Li, J. et al, Applied and Environmental Microbiology 61(12):4329-4333, 1995 also isolated the compound, but from a different bacterial strain and further demonstrated fungicidal activity. The fungicidal activity was also identified in a PCT application filed by Agro Biotech, in WO 1995/003695. The compound was further described in WO 2001/042231, Welichem Biotech as a protein kinase inhibitor. The compound has been in development by Welichem Biotech as WBI-1001 for the treatment of psoriasis and atopic dermatitis.

While the insecticidal, bactericidal, and fungicidal activity of 3,5-Dihydroxy-4-isopropyl-trans-stilbene has been well studied, its use against *P. Acnes* has not been. Given the history of compound 1, it would readily be believed to be active against *P. acnes*, but as can be seen below in the experimental section, it is not. The other known mode of action of the compound, e.g. as a protein kinase inhibitor would also not lead one skilled in the art to believe that this compound would be suitable for use in the treatment of acne. Thus, it is an unexpectant finding that 3,5-Dihydroxy-4-isopropyl-trans-stilbene is useful for the treatment of acne.

The compound 3,5-Dihydroxy-4-isopropyl-trans-stilbene has now been found to be an inhibitor of the Th 17 molecular pathway. It is by this mode of action that its use in the treatment of acne is established.

Th17 cells, a distinct Th lineage originally from the differentiation of naive CD4+ T cells, are potent inducers of tissue inflammation, and the hyperactivity of Th17 cells has been implicated in a variety of inflammatory and autoimmune disorders, such as psoriasis, rheumatoid arthritis and multiple sclerosis (Peck et al. Infect Immun, 78(1):32-38, 2010). At the molecular level, Th17 cells are characterized by the production of a distinct profile of effector cytokines including IL-17A and IL-17F. These cytokines activate different types of cells, such as keratinocytes, leading to their hyperproliferation and further production of proinflammatory cytokines, chemokines and antimicrobial peptides, which in turn recruit and activate other immune cells in the inflamed skin, leading to amplification of the inflammatory response.

Studies have shown that *P. acnes* and clinical isolates from acne patients are able to induce the differentiation of naïve CD4+ CD45RA T cells to IL-17 producing Th17 cells and to induce the secretion of IL-17A and IL-17F from human PBMC cells (Agak et al., J Invest Dermatol, advance online publication 12 Sep. 2013; doi: 10.1038/jid.2013.334). In addition, IL-17 expressing cells are found in the skin biopsies of acne patients, but not in the skin of healthy individuals, near the pilosebaceous follicles. These findings suggest that the induction of TH17 cells and the production of IL-17A and IL-17F play a key role in the pathogenesis of acne.

In addition, there is evidence that the down regulation or inhibition of inflammatory cytokines may have a beneficial effect for acne patients. Vitamin D and Vitamin A analogs, both used in the treatment of acne, have been shown to down regulate the expression of IL-17A and IL-17F in human PBMC cells in response to *P. acnes*, (See Agak et al., Supra.)

In view of this, topical and systemic drugs that inhibit the production of Th17 derived pro-inflammatory cytokines in the skin represent possible therapies against acne.

The mechanism of action of 3,5-Dihydroxy-4-isopropyl-trans-stilbene has not been fully elucidated to date. The anti-inflammatory activity of 3,5-Dihydroxy-4-isopropyl-trans-stilbene has been demonstrated both in a mouse ear edema model, with a dose dependent reduction in both skin redness and thickness, and in human trials for psoriasis and atopic dermatitis (See Bissonnette et al., Arch Dermatol, 146(4):446-449, 2010; Bissonette et al., Br. J. Dermatol., 166(4):853-860, 2012; and Bissonnette et al., J Eur Acad Dermatol Venereol, 26(12):1516-1521, 2012). Prior to this, the action of compound 3,5-Dihydroxy-4-isopropyl-trans-stilbene on IL-17 secretion from TH17 cells had not been demonstrated.

Thus, one aspect of the invention is the use of an effective amount of the compound 3,5-Dihydroxy-4-isopropyl-trans-stilbene, or a pharmaceutically acceptable salt thereof, for the treatment of acne. Another aspect is a method of treating acne with an an effective amount of the compound 3,5-Dihydroxy-4-isopropyl-trans-stilbene, or a pharmaceutically acceptable salt thereof. A further aspect of the invention provides the compound 3,5-Dihydroxy-4-isopropyl-trans-stilbene, or a pharmaceutically acceptable salt thereof, for use in the treatment of acne.

The present invention also provides for use of a pharmaceutical composition comprising 3,5-Dihydroxy-4-isopropyl-trans-stilbene, or a pharmaceutically acceptable salt thereof, and a pharmaceutically acceptable carrier or diluent, in the treatment of acne. Another aspect of the invention is a method of treating acne with an an effective amount of a pharmaceutical composition of 3,5-Dihydroxy-4-isopropyl-trans-stilbene, or a pharmaceutically acceptable salt thereof, and a pharmaceutically acceptable carrier or diluent. A further aspect of the invention provides a pharmaceutical composition comprising 3,5-Dihydroxy-4-isopropyl-trans-stilbene, or a pharmaceutically acceptable salt thereof, and a pharmaceutically acceptable carrier, for use in the treatment of acne.

Another aspect of the invention is the use of 3,5-Dihydroxy-4-isopropyl-trans-stilbene, or a pharmaceutically acceptable salt thereof, to suppress the production of IL-17A in a mammal in need thereof. Another aspect of the invention is suppression of the production of IL-17A in a mammal in need thereof, comprising administering to said mammal an effective amount of 3,5-Dihydroxy-4-isopropyl-trans-stilbene, or a pharmaceutically acceptable salt thereof.

Another aspect of the invention is the use of 3,5-Dihydroxy-4-isopropyl-trans-stilbene, or a pharmaceutically acceptable salt thereof, to induce keratinocyte cell death. Keratinocyte death would reduce keratinocyte hyperproliferation and comedome formation, thereby reducing follicle blockage and subsequent sebum retention in a blocked pore. Another aspect of the invention is inducing keratinocyte cell death in a mammal in need thereof, comprising comprising administering to said mammal an effective amount of 3,5-Dihydroxy-4-isopropyl-trans-stilbene, or a pharmaceutically acceptable salt thereof.

Another embodiment of the invention is the use of 3,5-Dihydroxy-4-isopropyl-trans-stilbene, or a pharmaceutically acceptable salt thereof, to suppress the production of IL-17A from cultured skin tissue challenged with a Th17-polarizing condition.

In one embodiment of the invention 3,5-Dihydroxy-4-isopropyl-trans-stilbene, or a pharmaceutically acceptable salt thereof, is applied topically in a concentration ranging from about 0.5% to about 5% w/w.

In another embodiment, 3,5-Dihydroxy-4-isopropyl-trans-stilbene, or a pharmaceutically acceptable salt thereof, is applied topically in a concentration of about 0.5% to about 2% w/w.

In another embodiment, 3,5-Dihydroxy-4-isopropyl-trans-stilbene, or a pharmaceutically acceptable salt thereof is applied topically in a concentration of about 0.5%, 1%, or 2% w/w.

In another embodiment 3,5-Dihydroxy-4-isopropyl-trans-stilbene, or a pharmaceutically acceptable salt thereof, is applied topically in a concentration of about 0.5% w/w.

In another embodiment 3,5-Dihydroxy-4-isopropyl-trans-stilbene, or a pharmaceutically acceptable salt thereof, is applied topically in a concentration of about 1.0% w/w.

In another embodiment 3,5-Dihydroxy-4-isopropyl-trans-stilbene, or a pharmaceutically acceptable salt thereof, is applied topically in a concentration of about 2.0% w/w.

In one embodiment of the invention 3,5-Dihydroxy-4-isopropyl-trans-stilbene, or a pharmaceutically acceptable salt thereof, is applied topically once or twice daily to the affected areas of a patient in need thereof.

In another embodiment 3,5-Dihydroxy-4-isopropyl-trans-stilbene, or a pharmaceutically acceptable salt thereof, is applied topically once daily to the affected areas of a patient in need thereof.

In another embodiment 3,5-Dihydroxy-4-isopropyl-trans-stilbene, or a pharmaceutically acceptable salt thereof, is applied topically twice daily to the affected areas of a patient in need thereof.

In one embodiment of the invention 3,5-Dihydroxy-4-isopropyl-trans-stilbene, or a pharmaceutically acceptable salt thereof, is applied topically in an amount from about 0.5% to about 5% w/w once or twice daily to the affected areas of a patient in need thereof.

As the biological profile of 3,5-Dihydroxy-4-isopropyl-trans-stilbene, and its pharmaceutically acceptable salts, differs from those of the currently-available products, this offers patients a novel therapeutic option for the treatment of acne. Although other topical treatment options are available, a novel topical medication that combines a high level of efficacy with an acceptable safety profile that would permit application to a large body surface area without restrictions on duration of treatment is still very much in need.

In one embodiment, the dosing frequency to the affected area(s) may be now be dosed less frequently than previously envisioned. Application of the 3,5-Dihydroxy-4-isopropyl-trans-stilbene, or a pharmaceutically acceptable salt thereof may be applied to affected areas twice daily, once daily, once every other day; twice weekly; three times weekly, or once weekly, with the dose represented by any of the embodiments herein. In another embodiment, the treatment may be administered in two phases, an initial dosage frequency such as once or twice daily, followed by a maintenance phase, such as every other day; twice weekly; three times weekly, or once weekly.

In another aspect of the invention the combination of 3,5-Dihydroxy-4-isopropyl-trans-stilbene, or a pharmaceutically acceptable salt thereof, administered with at least one additional therapeutic agent would provide two or more drivers with different modes of action, such as antibacterial, against the acne disease.

It is further expected that combinations of 3,5-Dihydroxy-4-isopropyl-trans-stilbene, or a pharmaceutically acceptable salt thereof with other therapeutic treatment regimens and products will be used. Therefore, in one embodiment 3,5-Dihydroxy-4-isopropyl-trans-stilbene, or a pharmaceutically acceptable salt thereof, is topically applied in combination with one or more secondary agents.

Various routes of administering the at least one or more therapeutic compounds to a subject are well known in the art, including but not limited to topical, oral, intradermal, intramuscular, intraperitoneal, intravenous, subcutaneous, intranasal, rectal, otic and ocular routes. In one embodiment, the administration of the second agent is topical or oral. In another embodiment the administration of the second agent is topical. It is expected that the second therapeutic agent would be also applied to the same local lesions over the body of the patient as the 3,5-Dihydroxy-4-isopropyl-trans-stilbene compound.

Suitably, the secondary agent is administered in a pharmaceutically or dermatologically acceptable composition. Suitable agents include, but not limited to, benzoyl peroxide, azelaic acid, dapsone, salicylic acid, tretinoin, adapalene, and other retinoic acid derivatives. Further, combination treatment with topical antibiotics, such as clindamycin phosphate, clinamycin, lincomycin, retapamullin, mupirocin, fusidic acid, tetracycline and its derivatives (e.g. Doxycycline, Minocycline, and Tetracycline), penicillin and its derivatives, and quinolone and all of its derivatives, including the fluoroquinolones class of compound are included herewith. Second therapeutic agents for use as an oral product to be used herein include but are not limited to isotretinoin, and the orally available antibiotics such as tetracycline and its derivatives (e.g. Doxycycline, Minocycline, and Tetracycline), including extended release versions thereof, penicillin and its derivatives, and quinolone and all of its derivatives, including the fluoroquinolones class of compound. All of the various permutations of their route of administration are intended to be covered herein.

The two or more medications may be administered together (depending upon the second therapeutic agent), sequentially, co-temperaneously or at alternative times, such as morning or night. The incorporation of a second therapeutic active into the same formulation, while contemplated, may be subject to the usual issues of stability and incompatibilities.

Consequently, 3,5-Dihydroxy-4-isopropyl-trans-stilbene, or a pharmaceutically acceptable salt may be used either together at the same time while in different formulations, or used sequentially or used co-temperaneously or even administered at completely alternative times, e.g. one in the morning and one at night with the usual agents available for acne treatment.

TERMS

As used herein the terms "modulate" or "modulates" refer to an increase or decrease in the amount, quality or effect of a particular activity.

As used herein, 'biological agents' means complex biological molecules such as antibodies, monoclonal antibodies, proteins, polypeptides and nucleotides.

As used herein, the term 'acne' includes truncal acne, facial acne, scalp acne, back acne, brachial acne, antebrachial acne, or leg acne.

As used herein, a 'treatment' for, or a 'method of treating', a medical condition, such as an acne condition, refers to a method of reducing, ameliorating or delaying the signs, symptoms, or progression of that medical condition. As used herein, 'treatment' does not imply a cure. A treatment need not be effective in every member of a population, e.g., a population of patients with acne, to have clinical utility, as is recognized in the medical and pharmaceutical arts.

As used herein, "treat", a 'treatment' for, or a 'method of treating' in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to an individual and interactions which would result in pharmaceutical compositions that are not pharmaceutically acceptable are avoided. In addition, each excipient must of course be of sufficiently high purity to render it pharmaceutically-acceptable.

As used herein, Th17 activating conditions refer to tissue culture conditions which result in the differentiation of T cells resident in the tissue into effector Th17 helper cells. As used herein, 'Th17 activation' is used interchangeably with the term 'Th17 stimulation'.

As used herein, 'subjects' and/or 'patients' includes human subjects and patients, including adult, teens and pediatric patients.

As used herein, 'topical' administration of a compound or medicament refers to application to and absorption through epithelial or mucocutaneous linings. In one aspect, topical application consists of or comprises application to the cutis or external integument of a subject, such as application to the epidermis of skin, including application to acne lesions. Appropriate vehicles and pharmaceutical carriers for use in topical application are known in the art.

In one embodiment, the term "pharmaceutically acceptable" means approvable by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic agent is administered.

It should be understood that the terms "a" and "an" as used herein refer to "one or more" or "at least one" of the enumerated components. It will be clear to one of ordinary skill in the art that the use of the singular includes the plural unless specifically stated otherwise.

The term "and/or" as used herein covers both additively and also alternatively the individual elements of a list which are thus linked so that these elements are to be understood as linked selectively with "and" or respectively with "or". Furthermore, the terms used in the singular of course also comprise the plural.

Throughout the application, descriptions of various embodiments use "comprising" language, however in some specific instances, an embodiment can be described using the language "consisting essentially of" or "consisting of".

An 'effective amount' of the compound or agent for treatment of a disease or condition can be determined by standard clinical techniques.

As used herein, "mammal" includes, but is not limited to, humans, including pediatric, adult and geriatric patients.

EXPERIMENTAL SECTION

Example 1: Effects of 3,5-Dihydroxy-4-Isopropyl-Trans-Stilbene on Peripheral Blood Derived CD4+ T Cells Skin-Resident Immune Cell Cytokine Production In this example, we investigate the ability of compound 1 to suppress the release of IL-17A from ex vivo human skin challenged with a pro-inflammatory Th17-skewing cocktail.

Stimulation of skin-resident immune cells in ex vivo human skin explants leads to the production of pro-inflammatory cytokines, including but not limited to IL-17A, IL-17F, and IL-22, thereby providing a novel model system with which to evaluate immunomodulatory therapeutics targeting skin inflammatory processes. Using this system, we show that 3,5-Dihydroxy-4-isopropyl-trans-stilbene can suppress IL-17A induction.

The ability of a test compounds to modulate the expression of pro-inflammatory cytokines was assessed using the skin-Resident Immune Cell Activation method. Ex vivo human skin obtained from abdominoplasty surgery was processed to remove fat and the tissue dermatomed to ~750 microns. Dermatomed skin was then cleaned in two serial rinses of 5-10 minutes each in room temperature PBS containing an antibiotic/antimycotic solution containing 1% Fungizone (Invitrogen), 50 µg/ml gentamicin (Invitrogen), and 0.5% PSG, for final concentrations of 100 U/ml Penicillin, 100 µg/ml streptomycin and 2 mM L-glutamine (Gibco). The section was cut with disposable single-use biopsy punches to 10 mm diameter round sections, which were then placed in the upper chamber of a 0.4 um PCF membrane transwell (Millicell # PIHP01250) containing 30 µl of a 64% bovine collagen solution (Organogenesis, #200-055). The skin samples were allowed to set on the collagen solution for 30 min at 37° C. Then, skin samples on transwells were transferred to 6-well plates (1 sample per well), and the lower chamber filled with 1 mL complete media (Cornification Media) and treated with or without 3,5-Dihydroxy-4-isopropyl-trans-stilbene.

On the last day of culture, skin tissue harvested into RNA later for analysis by qPCR (N=9 individual skin donors).

Skin-Resident Immune Cells were activated in situ under Th17-polarizing conditions, similar to conditions used in the literature for PBMCs. Specifically, human skin explants (triplicate samples per donor per condition) were stimulated with CD3 (2 µg/ml; clone UCHT1; BD Pharmingen) and CD28 (1 µg/ml; clone #37407; R&D Systems) antibodies in the culture medium to engage the T cell antigen receptor and provide co-stimulatory signals in the presence of Th17-polarizing conditions, which includes neutralizing antibodies directed against IFNγ (2 µg/ml; clone #25723; R&D Systems) and IL-4 (2 µg/ml; clone #3007; R&D Systems), recombinant human (rh) cytokines from R&D Systems, including rh IL-6 (10 ng/ml), rh IL-1b (10 ng/ml), and TGFβ (1 ng/ml), as well as rh IL-21 (10 ng/ml) from Southern-Biotech.

Total RNA was isolated from about 30-40 mg of tissue using Qiagen's (Cat #74106) Mini RNA Isolation kit. Tissue was homogenized in the Precellys-24 machine using 300 µL of RLT buffer supplemented with 1% 2-β-mercaptoethanol at 6300 rpm for 30 seconds for 9 cycles with a 2 min ice break every 3rd cycle. RNAse-free water (600 µl) containing Proteinase K was added to the homogenate and digested at 55° C. for 15 minutes. Digested tissue was spun down for 3 minutes at 10,000×g and the supernatant was used for RNA isolation using Qiagen's RNeasy mini columns according to the manufacturer's protocol. For each technical replicate, 100 ng of RNA was used as template in a 20 uL PCR volume using Applied Biosciences RNA-to-CT 1 Step kit (AB Catalog #4392938) as well as the specific TaqMan probe for each gene to be quantified. Applied Biosciences' Master Mix has a ROX dye internal control. OneStepPlus PCR machine was used for both the RT step and the 40 amplification cycles. Each gene was run in triplicate and the average Ct value used for calculating relative gene expression.

Relative gene expression data were averaged across triplicate biological replicates from PCR amplification run in technical triplicates. All data were normalized to untreated control samples (set to 1), and the average fold change (+/−SEM) calculated for each graph. Significant differences between treatment groups were identified by two-tailed Student's t test, p≤0.05.

Figure 1:
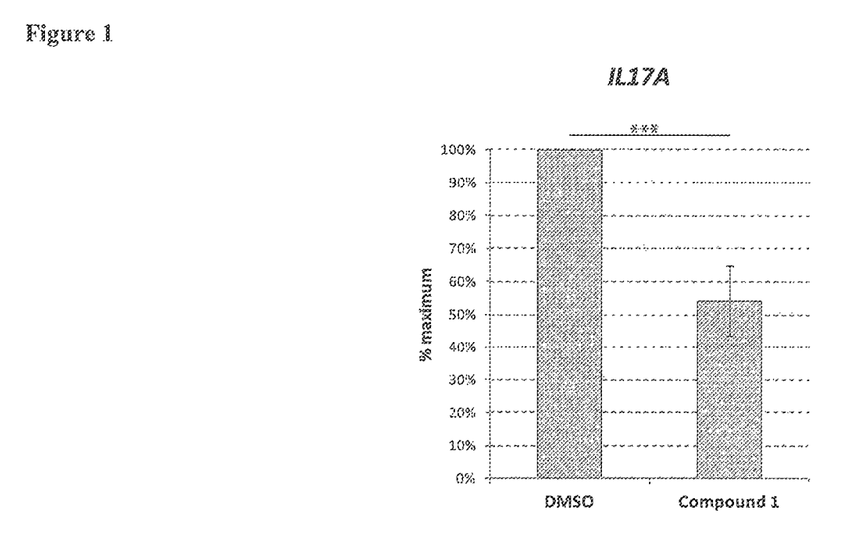
FIG. 1 shows that the transcript expression of IL-17A is inhibited with 1-day pretreatment of 3,5-Dihydroxy-4-isopropyl-trans-stilbene.

Stimulation of ex vivo human skin explants with antibodies and cytokines favoring T-helper cell-type 17 (Th17) differentiation, referred to throughout as Th17 conditions' or Th17 polarizing conditions', leads to a dramatic induction in transcript expression and protein secretion of the Th17-type cytokines, IL-17A and IL-17F. The compound 1 was examined to see if it affected cytokine expression in this model. One day of treatment prior to stimulation of skin-resident T cells under Th17-polarizing conditions reduced the level of IL-17A gene expression at 24 hrs post stimulation compared to control-stimulated explants cultures (FIG. 1). Relative transcript levels were determined using qPCR from whole RNA extracted from individual skin explants (N=3 per treatment group per donor) and quantified by the delta delta Ct method, which compares expression of the gene of interest (i.e., IL-17A gene expression) to an endogenous housekeeping control gene (i.e., beta-actin).

Figure 2:
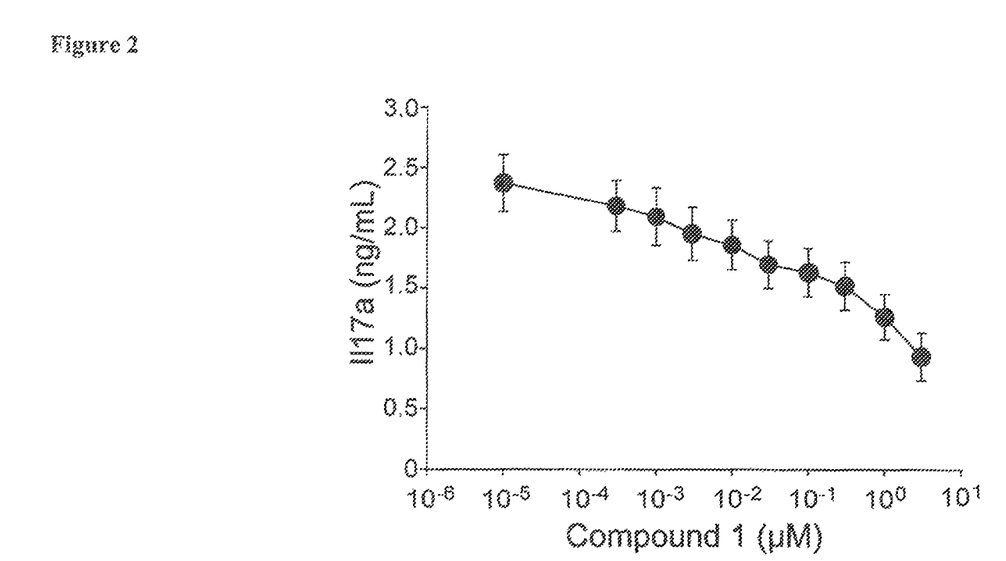
FIG. 2 shows the dose dependent effects by 3,5-Dihydroxy-4-isopropyl-trans-stilbene on IL-17A protein production.

To further understand the active dose range of compound 1-mediated suppression of Th17-associated cytokines, IL-17A protein secretion was examined in peripheral blood CD4+ T cells following 5 days of culture under Th17 polarizing conditions in the presence or absence of titrating doses of Compound 1 (FIG. 2). Supernatants were harvested at the end of the culture period and secreted protein was analyzed by Magpix (magnetic-based Luminex technology). In this experiment, IL-17A protein levels were suppressed by compound 1 in a dose-dependent manner.

As can be seen in FIG. 1, Experimental schema: compound 1 (10 µM)-induced inhibition of il17a gene expression of is shown relative to vehicle-treated (0.2% DMSO) samples (set to 100% such that inhibition across multiple skin donors could be compared. Compound 1 as used herein refers to 3,5-Dihydroxy-4-isopropyl-trans-stilbene.

FIG. 2 shows the dose dependent effects by compound 1 on IL-17A protein levels from Th17-polarized peripheral blood T cells.

The ability of compound 1 to suppress IL-17A in challenged ex vivo skin and peripheral blood CD4+ T cells supports the claim that compound 1 would be efficacious in the treatment of inflammatory skin conditions that require IL-17A secretion such as acne.

Figure 3:
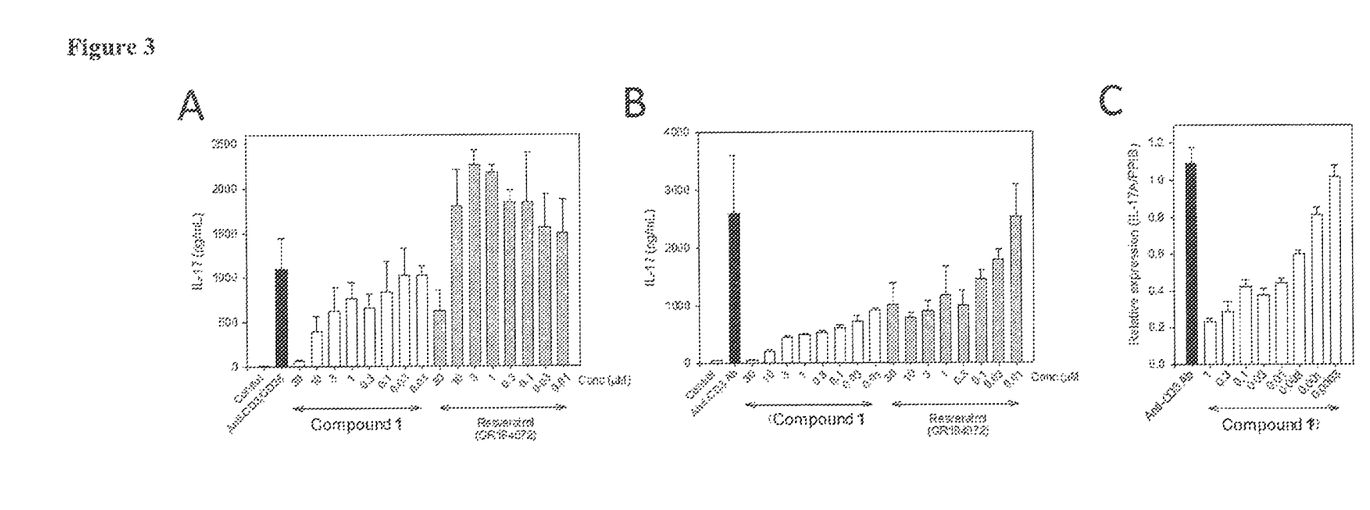

Example 2: Effect of 3,5-Dihydroxy-4-Isopropyl-Trans-Stilbene on Th17 Polarized Cells and on Th17 Cell Differentiation Treatment of pre-existing Th17 polarized cells with compound 1 for 24 hours showed reduced IL-17 secretion in a concentration dependent manner. Although activator beads resulted in greater increases in IL-17 release compared to immobilized anti-CD3, the inhibitory effect of 3,5-Dihydroxy-4-isopropyl-trans-stilbene was comparable for either TCR stimulus (FIG. 3).

At 30 µM the compound reduced IL-17 levels by 80-95% relative to stimulus alone. Resveratrol exerted a biphasic effect on IL-17 with partial inhibition only at 30 µM and enhancement at lower concentrations.

At 30 µM 3,5-Dihydroxy-4-isopropyl-trans-stilbene completely inhibited secretion of IL-17 and at 10 µM IL-17 was reduced by approximately 80%. At 100 nM 3,5-Dihydroxy-4-isopropyl-trans-stilbene, IL-17 secretion was suppressed by more than 60%. (FIG. 3 (A-B)). The compound inhibited IL-17A mRNA expression in parallel and at the same potency as secretion of IL-17 protein (FIG. 3 (C)).

CD4+ T cells were purchased from AllCells LLC as frozen vials.

As noted, FIG. 3 shows 3,5-Dihydroxy-4-isopropyl-trans-stilbene suppresses cytokine secretion by differentiated Th17 cells and potently inhibits the Th17 polarization of CD4+ T cells. In FIG. 3 (A): Differentiated Th17 cells were treated with compound 1 or resveratrol (0.01-30 µM) and stimulated with anti-CD3/CD28 beads. After 24 hours the concentration of IL-17 secreted into conditioned medium was determined. In FIG. 3 (B-C): CD4+ T cells were polarized to Th17 cells over a 5-day culture in the presence of Th17 polarization cocktail, anti-CD3 and CD28 antibodies, with or without compound 1 or resveratrol (0.01-30 µM). In FIG. 3 (B): Concentration-response curves for compound 1 expressed as total secreted IL-17A protein in pg/ml. In FIG. 3 (C): IL-17A mRNA expression normalized to PPIB. The results shown in FIG. 3 (A) are from a single experiment. Data in FIGS. 3 (B and C) are from a representative experiment repeated at least once with similar results.

CD4+ T cells were differentiated to the Th17 subtype by culturing for 5 days in vessels coated with anti-CD3 antibody (2 μg/mL) in Iscove's modified Dulbecco's medium (IMDM) containing 10% HI-FBS, 55 μM β-ME, soluble anti-CD28 (3 μg/mL) and a Th17 cytokine/anti-cytokine antibody cocktail of IL-10 (10 ng/mL), IL-6 (30 ng/mL), TGFβ (0.5 ng/mL), IL-21 (10 ng/mL), IL-23 (10 ng/mL), anti-IFNγ (10 μg/mL) and anti-IL-4 (10 μg/mL), essentially as described by Yang et al. Nature, 454(7202):350-352, 2008. To examine the effects of compounds on pre-existing Th17 polarized cells, polarizations 5-day culture period the cells were harvested, washed, and rested for 2 days in IMDM+10% HI-FBS. The cells were then seeded at 75,000 cells/well into round bottom 96-well plates either uncoated or coated with anti-CD3 and already containing serially diluted compounds. Cells dispensed into uncoated wells then received T-activator CD3/CD28 beads (1:1 ratio of beads:cells). All plates were cultured for 24 hours. To examine compound effects on Th17 polarization, freshly prepared CD4+ cells in IMDM supplemented with all Th17 polarization cocktail constituents (above) were seeded at low cell density (20,000 cells/well) directly into anti-CD3 coated round bottom 96-well plates already containing serially diluted compounds and cultured undisturbed for 5 days.

Example 3: The Effect of 3,5-Dihydroxy-4-Isopropyl-Trans-Stilbene on Lipogenesis in Sebocytes The effect of 3,5-Dihydroxy-4-isopropyl-trans-stilbene on modulation of lipogenesis in sebocytes was evaluated using an in vitro assay. Briefly, human immortalized sebocytes (tsSV40 and hTERT) were seeded and allowed to grow to confluence in Sebocyte Growth Medium. Upon confluence, cells were transferred to 37° C. to initiate Large T antigen degradation. Two days later, cells were stimulated with Sebocyte Labeling Medium containing 1 μM T0901317 and vehicle (DMSO) or compound 1. The compound 3,5-Dihydroxy-4-isopropyl-trans-stilbene was tested at concentrations of 10, 3, 1, 0.3 and 0.1 μM. Next day, the media was replaced with Sebocyte Labeling Medium containing 1 μM T0901317 and original treatments or vehicle plus 1 μM insulin. 2 ul of 14C-acetate was added per well and the plate incubated for 4 hours. After 2 hours of incubation, 10 ul of CTB reagent was added per well for normalization. Incubation was continued for the remaining 2 hours and plates were read at Ex. 560 Em.590 for CTB signal. Cells were then washed, trypsinized and transferred to glass vials for lipid extraction. The results are expressed as % lipid production relative to control (LXR+Insulin group).

As shown in

Figure 4:
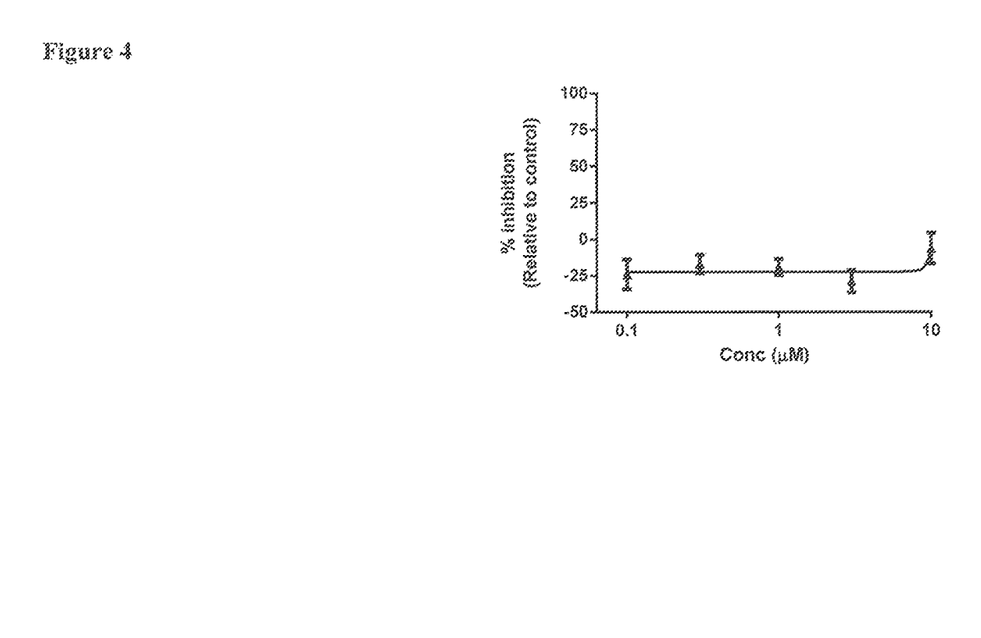
FIG. 4 shows 3,5-Dihydroxy-4-isopropyl-trans-stilbene not inhibiting sebum production.

FIG. 4, the data represent % inhibition relative to control (LXR+Insulin group). Data are represented as Mean±SEM. Data are from 3 replicates.

Compound 1 was found to be not active in the sebocyte lipogenesis assay. There were trends towards increased lipogenesis compound 1 in the sebocyte model relative to the control group (LXR+Insulin).

Figure 5:
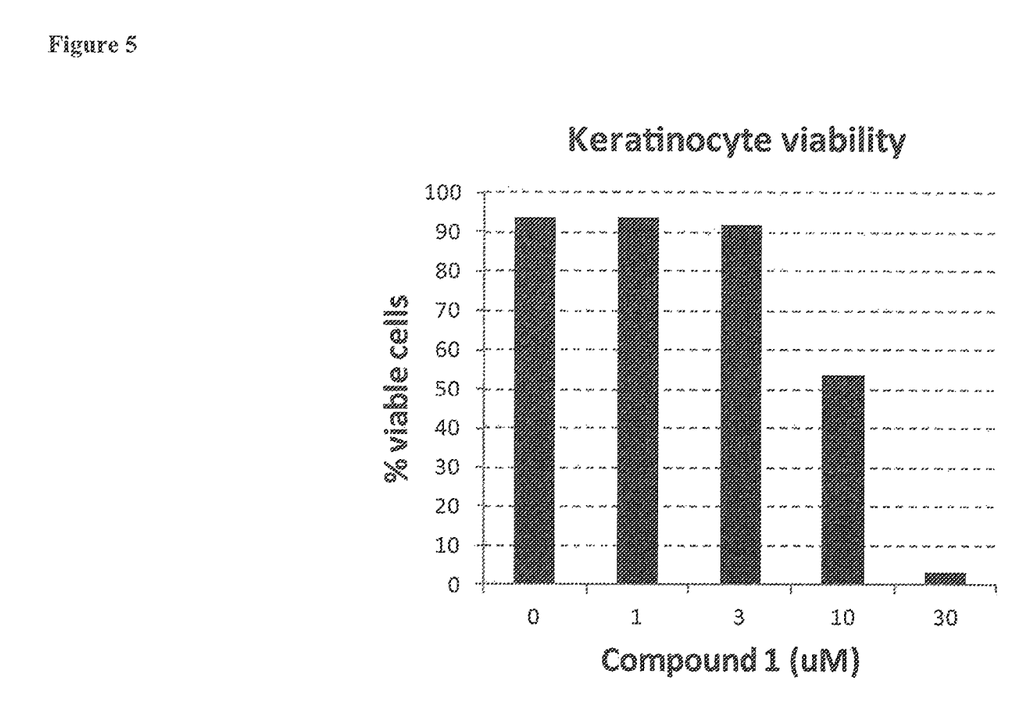
FIG. 5 shows the apoptoic effect of 3,5-Dihydroxy-4-isopropyl-trans-stilbene on primary keratinocytes.
Figure 6:
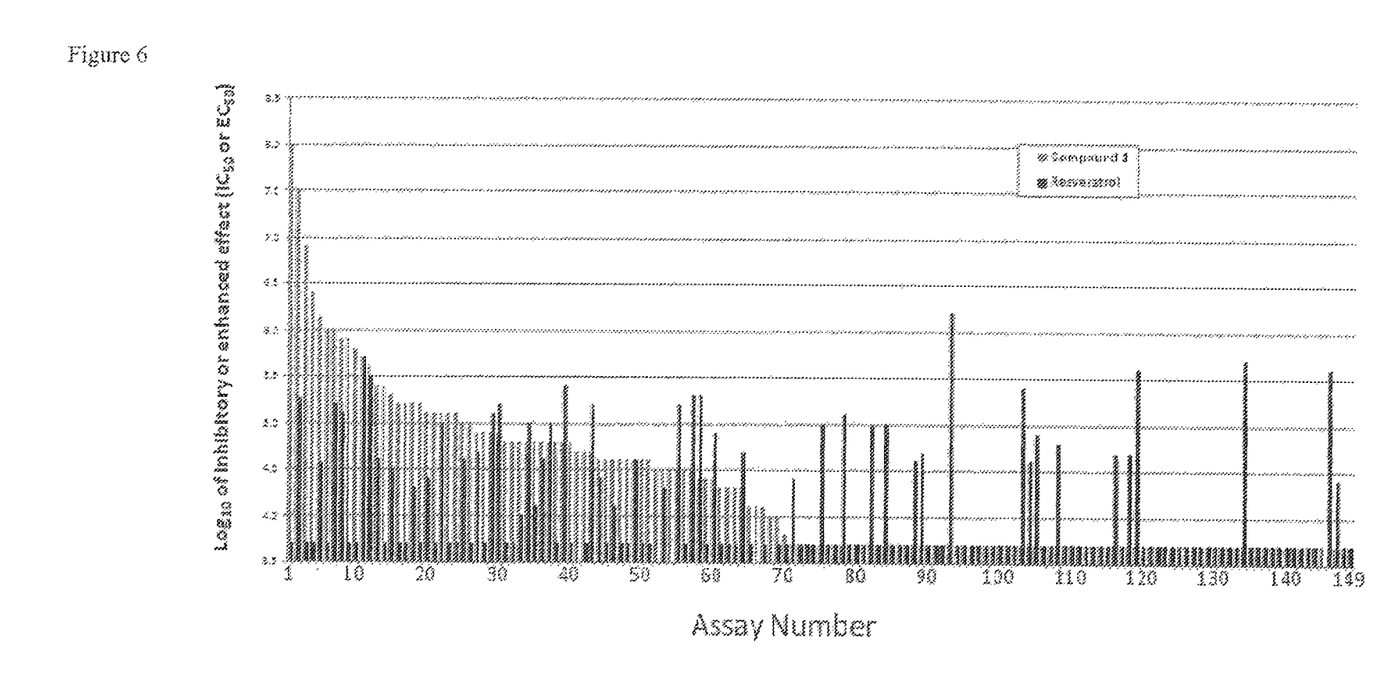
FIG. 6 compares the results of testing 3,5-Dihydroxy-4-isopropyl-trans-stilbene and resveratrol in a panel of 149 biochemical assays.

Example 4: The Effect of 3,5-Dihydroxy-4-Isopropyl-Trans-Stilbene on Keratinocyte Viability The effect of 3,5-Dihydroxy-4-isopropyl-trans-stilbene on keratinocyte viability was evaluated in vitro. Keratinocyte hyperproliferation increases blockage and can promote comedome formation in acne. Compound 1 was found to be overtly cytotoxic at 10 and 30 uM. The ability of Compound 1 to induce apoptosis in primary keratinocytes may contribute to efficacy in acne patients. The data is shown in FIG. 5.

Primary human keratinocytes were cultured in EpiLife medium containing HKGS growth supplement and seeded in tissue culture plates at 250,000 cells per plate. On the next day, the culture medium was removed and keratinocytes were then treated with culture medium containing vehicle control (DMSO) or increasing concentrations of Compound 1 (1, 10, 30 uM). After 48 hours of culture, keratinocytes were removed from tissue culture plates and cell viability was assessed by staining for apoptotic markers (annexin V and propidium iodide) using flow cytometry. The percentage of viable keratinocytes was quantitated as cells that did not stain for both apoptotic markers.

Example 5: Effects of 3,5-Dihydroxy-4-Isopropyl-Trans-Stilbene on P. Acnes

Bacterial strains utilized to evaluate this concept of antibacterial synergy were the clinical isolates P. acnes 6601, 6602, AN24, 100372, and reference strain ATCC6919. These were received from the internal culture GSK collection held by the Infectious Disease CEDD at the Upper Providence site. Bacteria inocula were prepared, and the determination of the minimal inhibitory concentration (MIC) were conducted on supplemented Brucella blood agar as described for the CLSI guideline method (Bhate, K. et al. Brit. J. Derm. 168:474-485, 2013). Briefly, diluted antibacterials were added to tempered molten agar and aseptically poured into petri dishes and allowed to solidify. Following 24-hours incubation in an anaerobic environment bacterial colonies were suspended and adjusted for turbidity equivalent to a 0.5 MacFarland standard. One-two microliters of inoculums were placed on each antibiotic containing agar plate and allowed to absorb for 30 min. Plates were then inverted and incubated anaerobically for 48-72 hours before observation for growth. The lowest drug concentration which inhibited bacterial growth was designated as the MIC.

MIC of 128 μg/ml was observed against all P. acnes strains tested for 3,5-Dihydroxy-4-isopropyl-trans-stilbene (Table 1).

TABLE 1

| MIC (μg/ml) of Compound 1 against P.acnes. | |
|---|---|
| | Compound 1 |
| 6601 | 128 |
| 6602 | 128 |
| AN24 | 128 |
| 100372 | 128 |
| ATCC6919 | 128 |

Based upon these results compound 1 would not be considered to be active as an antibacterial agent against P. acnes in contrast to true antibiotics like clindamycin with MICs<0.5 μg/ml against this bacterial species.

Example 6: Biological Profile of 3,5-Dihydroxy-4-Isopropyl-Trans-Stilbene Differs from that of Corticosteroids, Calcineurin Inhibitors, Vitamin D Analogs, and a Retinoic Acid Receptor Antagonist The effect of compound 1and other active agents that have been used in dermatological conditions, such as dexamethasone (low potency corticosteroid), fluticasone propionate (mid potency corticosteroid), clobetasol propionate (high potency corticosteroid), calcitriol (active form of vitamin D), tacrolimus (immunosuppressive drug), and a retinoic acid receptor antagonist (LE 135) were comparatively investigated in vitro across primary human cell types used in the Diversity Panel BioMAP system (Berg et al. Journal of Pharmacological and Toxicological Methods, 53(1):67-74, 2006).

The BioMAP™ Diversity Plus System employed included 12 assay systems which utilize specific combinations of human cells (endothelial cells, peripheral blood mononuclear cells, B cells, epithelial cells, T cells, macrophages, fibroblasts, keratinocytes and smooth muscle cells) stimulated with selected agents to mimic different disease states which activate multiple disease-relevant signaling pathways. A total of 148 phenotypic readouts (assays) were measured during this study. Compound 1 demonstrated its ability to modulate more than 25 biomarkers responsible for inflammatory, immune function, tissue remodeling and anti-proliferative activities, at one or more test concentration employed in this study. Measurement values for each parameter in a treated sample were divided by the mean value from eight DMSO control samples (from the same plate) to generate a ratio. All ratios were then log 10 transformed. Significance prediction envelopes were calculated for historical controls (99% and 95%). BioMAP™ profiles of 7 benchmark compounds Dexamethasone, Clobetasol propionate, Fluticasone propionate, Calcitriol, Tacrolymus (FK-506), SR-2111 (RORγ inverse agonist) and LE-135 (RAR antagonist) were compared against compound 1, and similar profiles were identified as those having Pearson correlations above a selected threshold>0.7. The profile of 3,5-Dihydroxy-4-isopropyl-trans-stilbene was found to be statistically significantly different, Pearson scores of less than or equal to 0.7, from that of Dexamethasone, Clobetasol propionate, Fluticasone propionate, Calcitriol, Tacrolymus (FK-506), SR-2111 (RORγ inverse agonist) and LE-135 (RAR antagonist) (Table 2). These results indicate that 3,5-Dihydroxy-4-isopropyl-trans-stilbene, or a pharmaceutically acceptable salt thereof is working through a mechanism of action distinct from that of the comparator compounds.

TABLE 2

| Comparator Compound | Pearson correlation score to Compound 1 |
|---|---|
| Dexamethasone | 0.03 |
| Clobetasol Propionate | 0.11 |
| Fluticasone Propionate | 0.20 |
| Calcitriol | −0.03 |
| FK-506 | 0.10 |
| SR2211 | 0.13 |
| LE135 | 0.25 |
| Resveratrol | 0.19 |

Given the structural similarity of the stilbene pharmacophore in resveratrol, a hydroxylated stilbene derivative produced by plants, Compound 1 was screened alongside resveratrol to assess their relative activity profiles. The activity profile of 3,5-Dihydroxy-4-isopropyl-trans-stilbene differs significantly from that of resveratrol as shown by the low Pearson correlation score between Resveratrol and Compound 1 (Table 2). To further confirm this, the two compounds were compared across a panel of 149 biochemical assays. There is little overlap in activity, and the two compounds present a different profile of activity (FIG. 5).

Therefore, the function and activity of Compound 1 cannot be predicted based on published literature regarding the activity of resveratrol.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A method of treating acne in a human in need thereof comprising topically administering to said human an effective amount of a compound which is 3,5-Dihydroxy-4-isopropyl-trans-stilbene, or a pharmaceutically acceptable salt thereof.

2. The method according to claim 1 wherein the acne is truncal acne.

3. The method according to claim 1 wherein acne lesions are affecting the facial and scalp areas of the human.

4. The method according to claim 1 wherein the compound is administered once daily to the affected areas of said human.

5. The method according to claim 1 wherein the compound is administered twice daily to the affected areas of said human.

6. The method according to claim 1 wherein the compound is 3,5-Dihydroxy-4-isopropy 1-trans-stilbene.

7. The method according to claim 1 wherein the compound is applied topically in a concentration ranging from 0.5% to 5% w/w.

8. The method according to claim 7 wherein the compound is applied topically in a concentration ranging from 0.5% to 2% w/w.

9. The method according to claim 8 wherein the compound is applied topically at 0.5%, 1%, or 2% w/w.

10. The method according to claim 1 wherein the compound is co-administered with an effective amount of a second therapeutic agent for the treatment of acne.

11. The method according to claim 10 wherein the co-administration of the second therapeutic agent is together at the same time, sequentially or contemporaneously with the 3,5-Dihydroxy-4-isopropyl-trans-stilbene, or a pharmaceutically acceptable salt thereof.

12. The method according to claim 11 wherein the 3,5-Dihydroxy-4-isopropyl-trans-stilbene, or a pharmaceutically acceptable salt thereof is administered at an alternative time to the second therapeutic agent.

13. A method of treating acne in a human in need thereof comprising topically administering to said human an effective amount of a pharmaceutical composition comprising 3,5-Dihydroxy-4-isopropyl-trans-stilbene, or a pharmaceutically acceptable salt thereof and a pharmaceutically acceptable carrier or diluent.

14. The method according to claim 13 wherein the acne is truncal acne.

15. The method according to claim 13 wherein acne lesions are affecting the facial and scalp areas of the human.

16. The method according to claim 13 wherein the compound is administered once daily to the affected areas of said human.

17. The method according to claim 13 wherein the compound is administered twice daily to the affected areas of said human.

18. The method according to claim 13 wherein the compound is 3,5-Dihydroxy-4-isopropy1-trans-stilbene.

19. The method according to claim 13 wherein the compound is applied topically in a concentration ranging from 0.5% to 5% w/w.

20. The method according to claim 19 wherein the compound is applied topically in a concentration ranging from 0.5% to 2% w/w.

21. The method according to claim 20 wherein the compound is applied topically at 0.5%, 1%, or 2% w/w.

22. The method according to claim 13 wherein the compound is co-administered with an effective amount of a therapeutic agent for the treatment of acne.

23. The method according to claim 22 wherein the co-administration of the second therapeutic agent is together at the same time, sequentially or contemporaneously with the 3,5-Dihydroxy-4-isopropyl-trans-stilbene, or a pharmaceutically acceptable salt thereof.

24. The method according to claim 23 wherein the 3,5-Dihydroxy-4-isopropyl-trans-stilbene, or a pharmaceutically acceptable salt thereof is administered at an alternative time to the second therapeutic agent.

25. The method according to claim 10 wherein the second therapeutic agent is administered orally or topically.

26. The method according to claim 22 wherein the second therapeutic agent is administered orally or topically.

27. The method according to claim 10 wherein the second therapeutic agent is selected from the group consisting of benzoyl peroxide, azelaic acid, dapsone, salicylic acid, tretinoin, adapalene, clindamycin phosphate, clinamycin, lincomycin, retapamullin, mupirocin, fusidic acid, tetracycline, doxycycline, minocycline, tetracycline, penicillin, quinolone, fluoroquinolones, isotretinoin, and any derivatives thereof.

28. The method according to claim 22 wherein the second therapeutic agent is selected from the group consisting of benzoyl peroxide, azelaic acid, dapsone, salicylic acid, tretinoin, adapalene, clindamycin phosphate, clinamycin, lincomycin, retapamullin, mupirocin, fusidic acid, tetracycline, doxycycline, minocycline, tetracycline, penicillin, quinolone, fluoroquinolones, isotretinoin, and any derivatives thereof.

29. The method according to claim 1 wherein the compound is administered every other day, twice weekly, three times weekly, or once weekly.

30. The method according to claim 13 wherein the compound is administered every other day, twice weekly, three times weekly, or once weekly.

* * * * *